(12) United States Patent
Wang et al.

(10) Patent No.: US 12,089,998 B2
(45) Date of Patent: Sep. 17, 2024

(54) ULTRASOUND IMAGING DEVICE AND SYSTEM AND BREAST ULTRASOUND APPARATUS

(71) Applicant: Chison Medical Technologies Co., LTD., Wuxi (CN)

(72) Inventors: Hong Wang, Wuxi (CN); San Cao, Wuxi (CN); Cheng Yang, Wuxi (CN); Yong Zhang, Wuxi (CN)

(73) Assignee: Chison Medical Technologies Co., LTD., Wuxi (CN)

( * ) Notice: Subject to any disclaimer, the term of this patent is extended or adjusted under 35 U.S.C. 154(b) by 0 days.

(21) Appl. No.: 17/423,175

(22) PCT Filed: Jan. 12, 2021

(86) PCT No.: PCT/CN2021/071228
§ 371 (c)(1),
(2) Date: Jul. 15, 2021

(87) PCT Pub. No.: WO2021/248910
PCT Pub. Date: Dec. 16, 2021

(65) Prior Publication Data
US 2023/0086369 A1    Mar. 23, 2023

(30) Foreign Application Priority Data
Jun. 10, 2020  (CN) .......................... 202010525364.7

(51) Int. Cl.
*A61B 8/08*         (2006.01)
*A61B 8/00*         (2006.01)
(Continued)

(52) U.S. Cl.
CPC .............. *A61B 8/5269* (2013.01); *A61B 8/06* (2013.01); *A61B 8/463* (2013.01); *A61B 8/5207* (2013.01);
(Continued)

(58) Field of Classification Search
CPC ......... A61B 8/5269; A61B 8/06; A61B 8/463; A61B 8/5207; A61B 8/5246; A61B 8/0825; A61B 8/14; A61B 8/486
See application file for complete search history.

(56) References Cited

U.S. PATENT DOCUMENTS 4,265,126 A    5/1981  Papadofrangakis et al.
4,679,565 A *  7/1987  Sasaki ................. G01S 7/52038
                                                    73/602

(Continued)

FOREIGN PATENT DOCUMENTS

CN    102429684 A    5/2012
CN    104143047 A    11/2014
EP       1548462 A1    6/2005

OTHER PUBLICATIONS

International Search Report for PCT/CN2021/071228, mailed on Apr. 9, 2021.
(Continued)

*Primary Examiner* — Oommen Jacob
(74) *Attorney, Agent, or Firm* — FINNEGAN, HENDERSON, FARABOW, GARRETT & DUNNER LLP (57) ABSTRACT

The present disclosure relates to the technical field of image processing, in particular to an ultrasound imaging device and system and a breast ultrasound apparatus. The ultrasound imaging device includes: a memory and a processor, the memory storing at least one program instruction, and the processor loading and executing the at least one program instruction to implement the following steps: transmitting ultrasound pulses and receiving n echo signals in an interleaved transmission and reception manner, wherein n is an integer greater than 1; acquiring a differential signal d(t) of the n echo signals; performing amplitude detection on the n echo signals to obtain an envelope of each echo signal, and
(Continued)

acquiring a sum B(t) of the envelopes of the echo signals; calculating image gray intensity of the blood flow imaging mode according to the d(t) and B(t); acquiring B-mode ultrasound echo data; and performing scan conversion on the B-mode ultrasound echo data and the calculated image gray intensity of the blood flow imaging mode, and displaying an ultrasound image according to a conversion result. In this way, the problem of artifacts in the ultrasound image in the prior art is solved. The present disclosure can be used to scan the breast and other organs and tissues.

20 Claims, 4 Drawing Sheets (51) Int. Cl.
*A61B 8/06* (2006.01)
*A61B 8/14* (2006.01)
(52) U.S. Cl.
CPC .......... *A61B 8/5246* (2013.01); *A61B 8/0825* (2013.01); *A61B 8/14* (2013.01); *A61B 8/486* (2013.01)

(56) References Cited

U.S. PATENT DOCUMENTS

| | | | | |
|---|---|---|---|---|
| 4,991,589 A | * | 2/1991 | Hongo | A61B 8/13 600/455 |
| 5,282,471 A | * | 2/1994 | Sato | G01S 15/8993 600/443 |
| 5,609,155 A | * | 3/1997 | Guracar | G01S 7/52066 600/453 |
| 5,860,931 A | * | 1/1999 | Chandler | A61B 8/06 600/458 |
| 6,146,330 A | * | 11/2000 | Tujino | G01S 7/52038 600/458 |
| 6,306,091 B1 | * | 10/2001 | Sumanaweera | G91S 15/8993 600/443 |
| 6,315,729 B1 | * | 11/2001 | Averkiou | G01S 7/52026 600/458 |
| 6,419,632 B1 | * | 7/2002 | Shiki et al. | G01S 15/8979 600/443 |
| 6,749,569 B1 | * | 6/2004 | Pellegretti | G01S 7/52074 600/441 |
| 6,978,876 B1 | * | 12/2005 | Tsukahara et al. | A61B 8/481 601/3 |
| 8,206,302 B2 | * | 6/2012 | Zhang et al. | G01S 15/8979 600/443 |
| 2008/0188751 A1 | | 8/2008 | Sato | |
| 2009/0209861 A1 | * | 8/2009 | Nishigaki et al. | A61B 8/06 600/455 |
| 2013/0281855 A1 | | 10/2013 | Baba et al. | |
| 2023/0086369 A1 | * | 3/2023 | Wang | A61B 8/5269 |

OTHER PUBLICATIONS

Extended European Search Report in counterpart European patent application No. EP21742291.4, dated Sep. 7, 2022.

* cited by examiner

ULTRASOUND IMAGING DEVICE AND SYSTEM AND BREAST ULTRASOUND APPARATUS

This application is a national stage filing under 35 U.S.C. § 371 of International Application No. PCT/CN2021/071228, filed Jan. 12, 2021, and claims the priority and benefit of Chinese Patent Application No. 202010525364.7, filed Jun. 10, 2020, which are incorporated herein by reference in their entireties.

TECHNICAL FIELD

The present disclosure relates to the technical field of image processing, in particular to an ultrasound imaging device and system and a breast ultrasound apparatus.

BACKGROUND

In ultrasound two-dimensional gray images, tissues or organs are imaged at different gray levels according to scattering intensity of reflectors or imaging points. In a two-dimensional gray image, blood in blood vessels appears black (without echo), while vascular walls are displayed as bright borders.

To enhance the display of blood cells in the gray image, a transmitted pulse level can be increased, so that the echo of the red blood cells is stronger. However, while the echo of the red blood cells is enhanced, the echo of surrounding tissues is also enhanced, that is, thermal noise and tissue signals are increased, and artifacts appear in a blood flow image. For example, the vascular walls appear colored.

A color blood flow mode is the most commonly used blood flow displaying mode in two-dimensional ultrasound images. In the color blood flow mode, two sets of different transmission signals are transmitted to simultaneously display the blood flow and surrounding tissues. One set of transmission signals is used for a gray image, and the other set is used for a blood flow image. When an ultrasound probe receives echo signals from the two sets of transmission signals, an ultrasound system processes the same separately to form the gray image and the blood flow image. Then the blood flow image is superimposed on the gray image, and the system generates a single display image.

However, in the color blood flow mode, due to the use of long transmission pulses and a method of superimposed display of the gray image and the blood flow image, the vascular walls appear colored, colors cover tissues, and artifacts of different colors appear on bright reflectors. How to remove artifacts has become a problem to be solved urgently by those skilled in the art when providing color blood flow images.

SUMMARY

In view of this, embodiments of the present disclosure provide an ultrasound imaging device and system and a breast ultrasound apparatus to solve the problem that artifacts appear in an ultrasound blood flow image in the existing solution. The present disclosure can be used to scan the breast, blood vessels and other organs and tissues.

According to a first aspect, an embodiment of the present disclosure provides an ultrasound imaging device, including: a memory and a processor, the memory storing at least one program, and the processor loading and executing the at least one program instruction to implement the following steps:

transmitting ultrasound pulses and receiving n echo signals in an interleaved transmission and reception manner in a blood flow imaging mode, wherein n is an integer greater than 1;

acquiring a differential signal d(t) of the n echo signals;

performing amplitude detection on the n echo signals to obtain an envelope of each echo signal, and acquiring a sum B(t) of the envelopes of the echo signals;

calculating image gray intensity of the blood flow imaging mode according to the d(t) and the B(t);

acquiring B-mode ultrasound echo data; and performing scan conversion on the B-mode ultrasound echo data and the calculated image gray intensity of the blood flow imaging mode, and displaying an ultrasound image according to a conversion result.

Optionally, the step of transmitting ultrasound pulses in an interleaved transmission and reception manner in a blood flow imaging mode includes:

enabling transmission and reception of a j-th group of receiving lines, wherein an initial value of j is 1; and setting j+1 after the reception of the j-th group of receiving lines is completed, and executing the step of enabling transmission and reception of the j-th group of receiving lines immediately.

Optionally, the step of calculating image gray intensity of the blood flow imaging mode according to the d(t) and the B(t) includes:

updating the value of the B(t) according to a magnitude relationship between the B(t) and a preset threshold $N_{thold}$; and calculating image gray intensity of the blood flow imaging mode according to the d(t) and the updated B(t).

Optionally, the step of updating the value of the B(t) according to a magnitude relationship between the B(t) and a preset threshold $N_{thold}$ includes:

regarding $N_{thold}$ as an updated B(t) if $B(t) < N_{thold}$.

Optionally, the step of calculating image gray intensity of the blood flow imaging mode according to the d(t) and the updated B(t) includes:

calculating image gray intensity of the blood flow imaging mode as $$\frac{|d(t)|}{|B(t)|};$$

or performing further processing as:

$$\log \frac{|d(t)|}{|B(t)|} = \log|d(t)| - \log|B(t)|.$$

Optionally, the step of performing scan conversion on the B-mode ultrasound echo data and the calculated image gray intensity of the blood flow imaging mode, and displaying an ultrasound image according to a conversion result includes:

combining the B-mode ultrasound echo data and an image of the blood flow imaging mode, and displaying the combined ultrasound image.

Optionally, the step of combining the B-mode ultrasound echo data and an image of the blood flow imaging mode, and displaying the combined ultrasound image includes: determining brightness of the combined ultrasound image according to a magnitude relationship between brightness of the image of the blood flow imaging mode and a brightness threshold, and the B-mode ultrasound echo data.

Optionally, the step of determining brightness of the combined ultrasound image according to a magnitude relationship between brightness of the image of the blood flow imaging mode and a brightness threshold, and the B-mode ultrasound echo data includes:

acquiring brightness $X_B$ of a B-mode ultrasound image and brightness $X_{S\text{-}Flow}$ of the image of the blood flow imaging mode;

determining that $X = X_B$ when $X_{S\text{-}Flow} \leq \text{threshold}_{S\text{-}Flow}$, wherein X is the brightness of the combined ultrasound image; and determining that $X = X_{S\text{-}Flow} + \alpha X_B / 256$ when $X_{S\text{-}Flow} > \text{threshold}_{S\text{-}Flow}$, wherein $\alpha$ is a coefficient, wherein $\text{threshold}_{S\text{-}Flow}$ is a minimum brightness level threshold of the blood flow imaging mode.

Optionally, $\alpha$ is one of:

$(a)\, \alpha = (256 - (X_{S\text{-}Flow} - \text{threshold}_{S\text{-}Flow}))$;

$(b)\, \alpha = 255 - \sqrt{255^2 - (X_{S\text{-}Flow} - \text{threshold}_{S\text{-}Flow} - 255)^2}$; and $(c)\, \alpha = 255 / (X_{S\text{-}Flow} - \text{threshold}_{S\text{-}Flow})$.

Optionally, the step of performing scan conversion on the B-mode ultrasound echo data and the calculated image gray intensity of the blood flow imaging mode, and displaying an ultrasound image according to a conversion result includes:

displaying a B-mode ultrasound image according to the B-mode ultrasound echo data; and displaying a blood flow image according to the image gray intensity of the blood flow imaging mode.

Optionally, the method further includes:

obtaining B-mode receiving lines and blood flow imaging mode receiving lines alternately until a complete B-mode image and blood flow imaging mode image is obtained when the n echo signals and the B-mode ultrasound echo data are acquired.

Optionally, the method further includes:

obtaining one frame of B-mode image and multiple frames of blood flow imaging mode images alternately when the n echo signals and the B-mode ultrasound echo data are acquired.

In a second aspect, an ultrasound system is provided, the ultrasound system including the ultrasound imaging device of the first aspect.

In a third aspect, a breast ultrasound apparatus is provided, the breast ultrasound apparatus including the ultrasound imaging device of the first aspect, the breast ultrasound apparatus being used to achieve the following functions:

transmitting ultrasound pulses to a breast area and receiving n echo signals in an interleaved transmission and reception manner in a blood flow imaging mode, wherein n is an integer greater than 1;

acquiring a differential signal d(t) of the n echo signals;

performing amplitude detection on the n echo signals to obtain an envelope of each echo signal, and acquiring a sum B(t) of the envelopes of the echo signals;

calculating image gray intensity of the blood flow imaging mode according to the d(t) and the B(t);

acquiring B-mode ultrasound echo data; and performing scan conversion on the B-mode ultrasound echo data and the calculated image gray intensity of the blood flow imaging mode, and displaying a breast ultrasound image according to a conversion result.

In the present disclosure, after the differential signal d(t) of the n echo signals and the sum B(t) of the envelopes of the echo signals are calculated, the image gray intensity of the blood flow imaging mode is calculated according to d(t) and B(t), and the ultrasound image is display according to the B-mode ultrasound echo data and the calculated image gray intensity during ultrasound imaging. In this way, the problem of artifacts in the ultrasound image in the prior art is solved, and artifacts in the image caused by tissue movement flickering and weak blood flow can be eliminated. The present disclosure can be used to scan the breast and other organs and tissues.

BRIEF DESCRIPTION OF THE DRAWINGS

In order to describe the technical solutions in the embodiments of the present disclosure or in the prior art more clearly, a simple introduction on the accompanying drawings used in the description of the embodiments or the prior art is given below. Apparently, the accompanying drawings in the description below are merely some of the embodiments of the present disclosure, based on which other drawings may be obtained by those of ordinary skill in the art without creative work.

DETAILED DESCRIPTION

The present disclosure is further described below specifically in conjunction with the accompanying drawings and embodiments.

To make the objects, technical solutions and advantages of the embodiments of the present disclosure clearer, a clear and complete description of the technical solutions in the embodiments of the present disclosure will be given below in conjunction with the drawings in the embodiments of the present disclosure. Apparently, the embodiments described are part of, but not all of, the embodiments of the present disclosure. All other embodiments obtained by those skilled in the art based on the embodiments of the present disclosure without creative work fall into the protection scope of the present disclosure.

Figure 1:
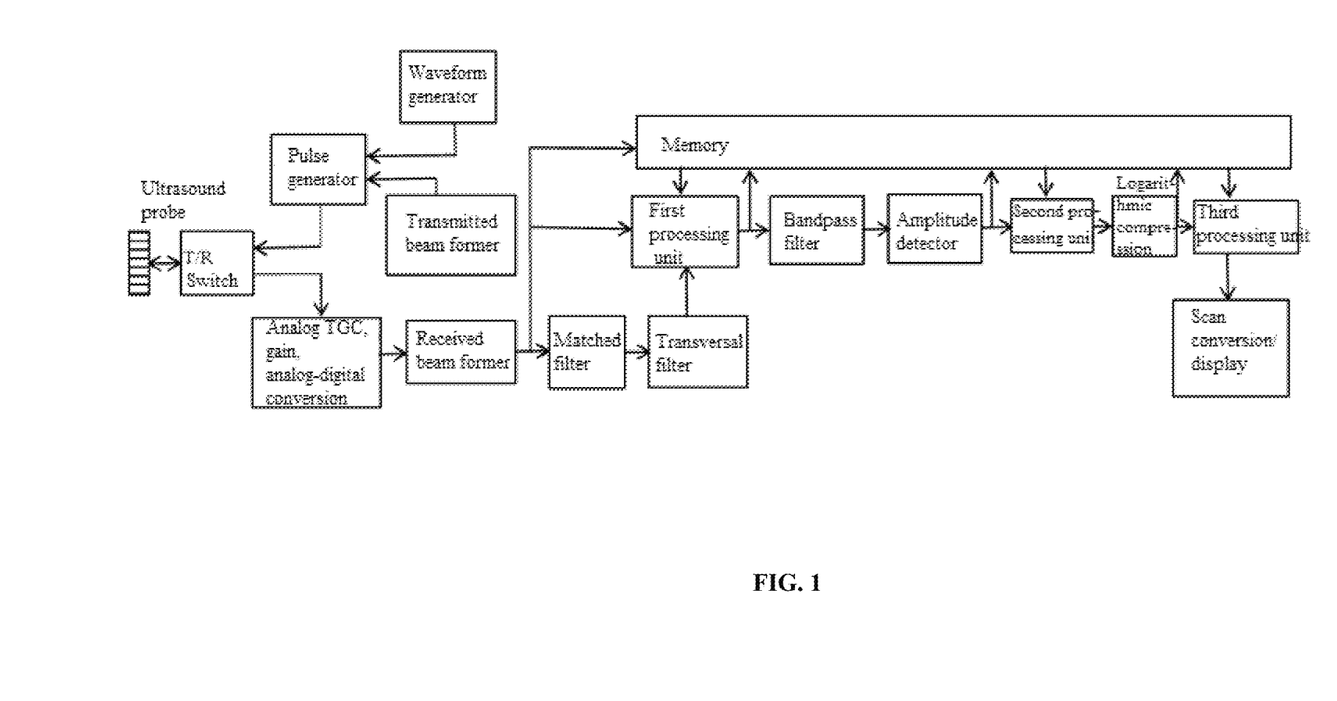
FIG. 1 is a structure diagram of an ultrasound apparatus according to some embodiments of the present disclosure.

To facilitate understanding, the related art of the present disclosure is first introduced briefly. The solution of the present disclosure is applied to an ultrasound apparatus. As shown in FIG. 1, the ultrasound apparatus includes the following components:

A waveform generator: configured to generate a data signal, so that a pulse generator generates a transmission pulse according to the data signal.

A transmitted beam former: configured to implement electronic focusing and control over a sound beam from a multi-array-element ultrasound probe. It appropriately delays a transmitted signal for each array element, so that transmitter signals reach a target at the same time and produce the highest sound intensity at the target, that is, a strongest echo signal is obtained.

A pulse generator: configured to generate a transmission pulse.

A T/R switch: a transmit-receive switch configured to control the ultrasound probe to be currently in a transmission mode or reception mode.

An ultrasound probe: composed of a piezoelectric element, a connector and a supporting structure. The ultrasound probe converts electrical energy into mechanical energy in the transmission mode, and a mechanical wave generated is propagated to a medium. In the reception mode, a reflected mechanical waveform is received, and converted into an electrical signal by the ultrasound probe.

A TGC (Time Gain Compensate) gain: an amplifier gain is controlled to increase with the deepening of a detection depth to compensate for attenuation of an ultrasound signal with a propagation distance.

An analog-digital converter: configured to convert an analog signal into a digital signal.

A received beam former: similar to the transmitted beam former, configured to implement electronic focusing and control over the sound beam from the multi-array-element ultrasound probe. It appropriately delays the received echo to implement linear superimposition of echo signals from multiple array elements to achieve the highest sensitivity.

A matched filter: a filter matched with transmission codes to achieve compression of the codes.

A transversal filter: configured to perform range sidelobe suppression on a received signal.

A first processing unit: configured to implement an addition, subtraction or bypass function. Bypass means that an information flow directly enters the next functional module.

A memory: configured to cache data, for example, caching a received echo signal or a processed echo signal. In actual implementation, the memory may be a volatile memory, such as random-access memory (RAM); the memory may also include a non-volatile memory, such as a flash memory, a hard disk drive (HDD) or a solid-state drive (SSD); and the memory may also include a combination of the above types of memory.

A bandpass filter: configured to selectively filter out a desired frequency band from the received signal.

An amplitude detector: configured to detect the amplitude of the received signal.

A second processing unit: configured to implement addition and bypass functions.

A logarithm compressor: configured to perform logarithmic operations on the received signal.

A third processing unit: configured to implement a subtraction or bypass function.

A scan convertor/display: configured to perform data conversion and then display an ultrasound image.

Referring to FIG. 1, in a B-mode, the waveform generator generates a required broadband pulse. The pulse is appropriately delayed by the transmitted beam former before entering the pulse generator. Then, the pulse generator generates a high-voltage pulse and sends it to the ultrasound probe. In B-mode reception, echo signals from the ultrasound probe are first amplified by the TGC (Time Gain Compensate) gain, and then converted into digital signals by the analog-digital converter, and the digital signals are delayed and added together by the received beam former. Beamforming may be implemented by one receiving line or a plurality of receiving lines. For a fundamental wave B-mode image, beamformed data directly enter the bandpass filter, that is, the first processing unit in the figure implements the bypass function (the bypass function described in this embodiment means skipping this unit and entering the next unit for processing), and the beamformed data directly enter the bandpass filter. For a tissue harmonic image, there are two transmission pulses with opposite phases. Beamforming data from a first pulse are stored in the memory. When beamforming data from a second pulse appear, the system adds the beamforming data from the two pulses together, that is, the first processing unit in FIG. 1 implements the addition function. In this way, fundamental wave signals of the beamforming data from the two pulses are eliminated, and second harmonic signals are added together, the sum of the second harmonic signals enters the bandpass filter, and a signal processed by the bandpass filter is subjected to scan conversion processing.

For a blood flow imaging mode, the waveform generator generates a coded pulse according to a predetermined code sequence, usually binary phase codes, such as Barker codes or Golay paired codes. The coded pulse is appropriately delayed by the transmitted beam former before entering the pulse generator. Then, the pulse generator generates a high-voltage coded pulse and sends it to the ultrasound probe. An echo signal received from the ultrasound probe is first amplified by the TGC, and then converted into a digital signal by the analog-digital converter. Since the transmitted pulse is coded, the echo signal received by the probe contains coded information, that is, the signal is a coded echo signal. These digitized coded echo signals are delayed and added together by the received beam former.

In the case where the coding sequence is Barker codes, a pulse compression (or decoding) process of the beamforming data is implemented by a matched filter and a transversal filter. The RSL (Range Sidelobe) level of the matched filter Barker codes is a few decibels lower than a main peak, and thus the transversal filter is provided to reduce the RSL to 30 decibels or lower, that is, the transversal filter is used to achieve range sidelobe suppression. The decoded signal may be stored in the memory, and may also be subjected to addition, subtraction or bypass processing by the first processing unit. In the case where the transmission coding sequence is Golay paired codes, a pair of Golay codes is transmitted separately, and a pulse compression process of the beamforming data is a matching and summing process by the matched filter. A first Golay-coded beamforming data are subjected to matched filtering and stored in the memory. A second Golay-coded beamforming data are matched, filtered and summed with the first data in the memory. As the summation process balances out the RSL, the transversal filter is bypassed. Using the Barker codes has the advantage of a single transmission operation, but requires an additional filter to suppress the RSL. Using the Golay paired codes can completely balance out the RSL, but requires two transmission operations, which reduces the frame rate.

After the addition, subtraction or bypass processing by the first processing unit, the echo signals in the B-mode and the blood flow imaging mode are subjected to bandpass filtering. The bandpass filter keeps the echo signals in a required frequency band and suppresses noise outside the frequency band, which is conducive to improving the signal-to-noise ratio. Then, the amplitudes of the echo signals are calculated by removing a carrier frequency. The detected amplitudes may be stored in the memory, and may also be summed by the second processing unit. Next, the processed data are output by the second processing unit and stored in the memory. Of course, the third processing unit may also be used for subtraction/bypass processing. After the above processing is carried out and the B-mode ultrasound echo data and the blood flow imaging mode data are obtained, the B-mode ultrasound echo data and the blood flow imaging mode data can be subjected to scan conversion and transmitted to a display for display.

In various embodiments herein, the first processing unit, the second processing unit and the third processing unit may respectively correspond to processors, or at least two processing units may correspond to one processor, which is not limited in this embodiment.

Figure 2:
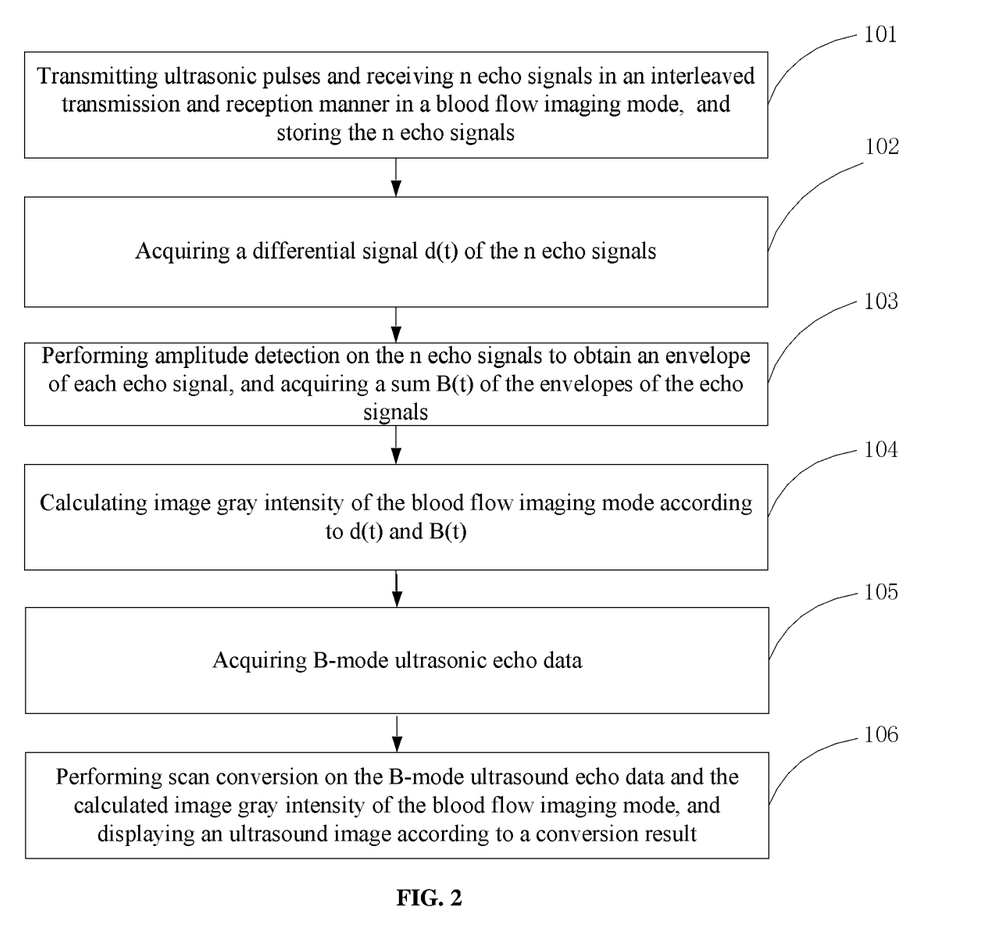
FIG. 2 is a method flow chart of an ultrasound imaging method according to some embodiments of the present disclosure.

FIG. 2 shows a method flow chart of an ultrasound imaging method according to some embodiments of the present disclosure, which is used in the ultrasound apparatus shown in FIG. 1. As shown in FIG. 2, the method includes the following steps. At step 101, ultrasound pulses are transmitted and n echo signals are received in an interleaved transmission and reception manner in a blood flow imaging mode, and the n echo signals are stored.

The ultrasound apparatus sets pulse repetition time PRT between two consecutive transmission operations to $\tau$ according to a blood flow velocity. A minimum PRT ($\tau_{min}$) is equal to the time required for one transmission and reception operation. Generally, to detect slow blood flow movement, such as blood entering arteriola and capillaries from major blood vessels, or, in detection of venous blood flow, $\tau$ needs to be increased so that a change of a phase of a Doppler frequency shift signal from one pulse to the next pulse can be measured. However, simply increasing $\tau$ will reduce the frame rate of the ultrasound image and decrease the signal-to-noise ratio. Therefore, in conjunction with FIG. 3, pulse signals are transmitted in an interleaved transmission manner in this embodiment.

Figure 3:
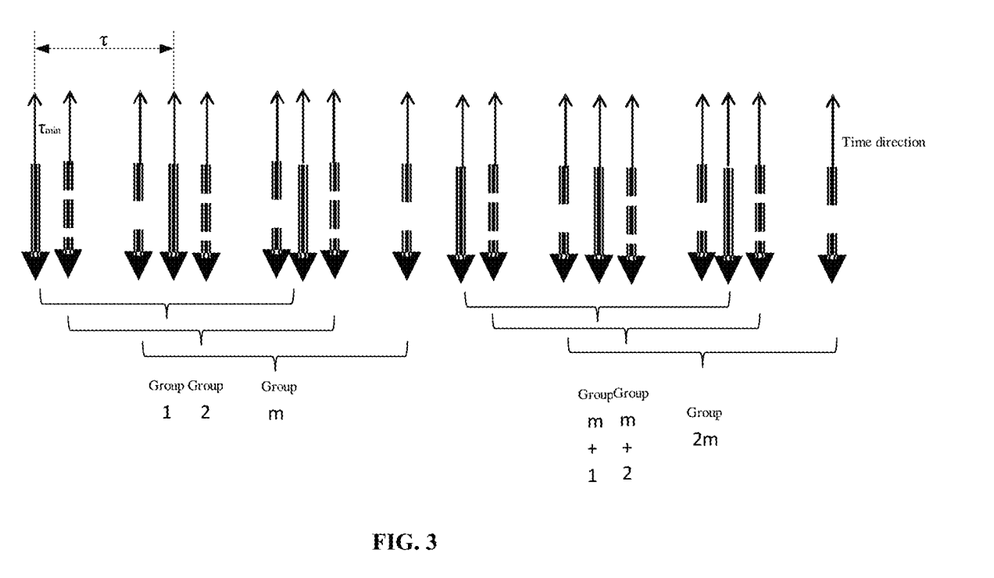
FIG. 3 is a schematic diagram of interleaved transmission of ultrasound pulses according to some embodiments of the present disclosure.

The ultrasound probe enables a first transmission and reception operation of a first group of receiving lines. The number of receiving lines in each group is i, wherein i≥1, and reception of the first group of receiving lines is completed after waiting time $\tau_{min}$. The ultrasound probe enables a transmission and reception process for a second group of receiving lines without waiting for the time $\tau$. The ultrasound probe operates in such a repeated manner until a first transmission and reception operation of an m-th group of receiving lines is completed. Then, the ultrasound probe enables a second transmission and reception operation of the first group of receiving lines, and operates in such a repeated manner until a second transmission and reception operation of the m-th group is completed. This process continues until an n-th transmission and reception operation of the m-th group of receiving lines. Then, the ultrasound probe moves to an (m+1)th group of receiving lines, and repeat the interleaving process in a similar transmission and reception manner as described above.

An echo signal is e(t)=A(t)cos (w₀t), wherein w₀ is an angular frequency of a pulse, and A(t) is an envelope signal. When n ultrasound pulses are transmitted successively, echo signals of the n ultrasound pulses are $e_1(t), e_2(t), \ldots, e_n(t)$, respectively.

In actual implementation, there may be loss after the ultrasound pulses are transmitted, so that the echo signals cannot be received. Therefore, in this embodiment, the number of ultrasound pulses transmitted may be greater than the number of echo signals received, and this is not limited here.

In addition, in the present disclosure, ultrasound pulses may be transmitted to the breast, blood vessels, or any tissue in the above-mentioned interleaved transmission and reception manner, which is not limited in this embodiment.

At step 102, a differential signal d(t) of the n echo signals is acquired.

When n is 2, $$d(t) = e_1(t) - e_2(t) = 2A(t)\sin\left(w_0\frac{v\tau}{c}\right)\sin\left(w_0\left(t + \frac{v\tau}{c}\right)\right);$$

and
when n is 3, $$d(t) = e_1(t) - 2e_2(t) + e_3(t) = -4A(t)\sin^2\left(w_0\frac{v\tau}{c}\right)\cos\left(w_0\left(t + \frac{v\tau}{c}\right)\right),$$

wherein c is a sound speed, $\tau$ is pulse repetition time, v is a moving speed of a moving target (which may be a blood flow in the present disclosure) in a beam direction, and A(t) here is an envelope signal for displaying reflecting intensity or scattering intensity of the target tissue.

When n=2, echo signals $e_1(t)$ and $e_2(t)$ formed by two beams can be received after two coded pulses are transmitted. After TGC gain and analog-digital conversion, referring to the above description, in the case where Barker codes are used for coded transmission, the echo signals are filtered by the matched filter and subjected to range sidelobe suppression by the transversal filter, and in the case of Golay-coded transmission, the echo signals are only filtered by the matched filter, and bypass the transversal filter, and $e_1(t)$ subjected to the above processing is stored in the memory. Subsequently, after $e_1(t)$ is filtered by the bandpass filter, amplitude detection is performed to obtain $|e_1(t)|$, which is then stored in the memory. After $e_2(t)$ is subjected to the above processing, the first processing unit executes subtraction $e_1(t)-e_2(t)$ by calling $e_1(t)$ from the memory to obtain d(t), and after d(t) is calculated, d(t) is stored in the memory.

When n=3, the ultrasound probe transmits three coded pulses and receives echoes $e_1(t)$, $e_2(t)$ and $e_3(t)$ formed by three beams. After $e_1(t)$ is processed the processed $e_1(t)$ is stored in the memory, and at the same time, is subjected to amplitude detection to obtain $|e_1(t)|$ after being filtered by the bandpass filter, which is then stored in the memory. After $e_2(t)$ is processed, in conjunction with FIG. 1, the first processing unit calculates $e_1(t)-2e_2(t)$ by calling $e_1(t)$ from the memory and stores the result in the memory. At the same time, $e_2(t)$ is subjected to amplitude detection to obtain $|e_2(t)|$ after being filtered by the bandpass filter. After $e_3(t)$ is processed, filtered by the bandpass filter and subjected to amplitude detection, the first processing unit adds $e_3(t)$ to $e_1(t)-2e_2(t)$ in the memory to implement second-order filtering of $e_1(t)-2e_2(t)+e_3(t)$ to obtain d(t).

At step 103, amplitude detection is performed on the n echo signals to obtain an envelope of each echo signal, and a sum B(t) of the envelopes of the echo signals is acquired; when n=2, $$B(t) = A(t) + A(t + \delta t) \approx 2A(t);$$

when n is 3, B(t)≈3A(t).

In actual implementation, when n=2, $e_1(t)$ is processed and then stored in the memory. After $e_2(t)$ is obtained, $e_2(t)$ is filtered by the bandpass filter and subjected to amplitude detection to obtain $|e_2(t)|$. In conjunction with FIG. 2, the second processing unit adds $|e_2(t)|$ to $|e_1(t)|$ stored in the memory to obtain $|e_1(t)|+|e_2(t)|$, thereby obtaining B(t).

Similarly, when n=3, $e_1(t)$ is processed and then stored in the memory, and at the same time, $e_1(t)$ is subjected to amplitude detection to obtain $|e_1(t)|$, which is then stored in the memory. After $e_2(t)$ is processed, $e_2(t)$ is filtered by the bandpass filter and then subjected to amplitude detection to obtain $|e_2(t)|$, which is then stored in the memory. After $e_3(t)$ is obtained, $e_3(t)$ is filtered by the bandpass filter and subjected to amplitude detection to obtain $|e_3(t)|$, and then the second processing unit adds $|e_2(t)|$ and $|e_1(t)|$ in the memory together to obtain $|e_1(t)|+|e_2(t)|$, and $e_1(t)|+|e_2(t)|$ is also stored in the memory. The second processing unit adds $|e_3(t)|$ to $|e_1(t)|+|e_2(t)|$ in the memory to obtain $|e_1(t)|+|e_2(t)|+|e_3(t)|$.

At step 104, image gray intensity of the blood flow imaging mode is calculated according to d(t) and B(t).

This step includes: calculating image gray intensity $$\frac{|d(t)|}{|B(t)|}$$

of the blood flow imaging mode as $$\frac{|d(t)|}{|B(t)|} \approx \frac{2A(t)\sin\left(w_0 \frac{v\tau}{c}\right)\sin\left(w_0\left(t + \frac{v\tau}{c}\right)\right)}{2A(t)} = \sin\left(w_0 \frac{v\tau}{c}\right)\sin\left(w_0\left(t + \frac{v\tau}{c}\right)\right).$$

It can be seen from the above description that the gray intensity of the echo signals in the blood flow imaging mode is irrelevant to A(t). Therefore, tissue movement flickering and weak blood flow caused by A(t) can be eliminated by the above acquisition method.

Optionally, in calculation of $$\frac{|d(t)|}{|B(t)|},$$

logarithmic compression can also be performed on $$\frac{|d(t)|}{|B(t)|},$$

and the image gray intensity is represented by a value after the logarithmic compression.

$$\log \frac{|d(t)|}{|B(t)|} = \log|d(t)| - \log|B(t)|.$$

That is, when n=2, the image gray intensity $\log(|e_1(t)-e_2(t)|)-\log(|e_1(t)|+|e_2(t)|)$ of the blood flow mode is obtained by the third processing unit. When n=3, the image gray intensity $\log(|e_1(t)-2e_2(t)+e_3(t)|)-\log(|e_1(t)|+|e_2(t)|+|e_3(t)|)$ of the blood flow mode is obtained by the third processing unit.

The above description is just an example of calculating the image gray intensity of the blood flow imaging mode in the above-mentioned manner. In actual implementation, this step includes:

First, the value of the B(t) is updated according to a magnitude relationship between the B(t) and a preset threshold $N_{thold}$.

When n=2, $|e_1(t)|+|e_2(t)|$ corresponds to the preset threshold $N_{thold}$, and if $B(t)<N_{thold}$, B(t) is replaced with $N_{thold}$;

and similarly, when n=3, if $B(t)<N_{thold}$, B(t) is replaced with $N_{thold}$. By setting the above preset threshold, noise in B-mode ultrasound can be suppressed, and the noise is prevented from being amplified and displayed in an image of the blood flow mode.

Second, image gray intensity of the blood flow imaging mode is calculated according to the d(t) and the updated B(t).

After B(t) is updated, the image gray intensity of S-Slow can be calculated according to d(t) and the updated B(t). The specific calculation method is as described above, and will not be repeated here.

In addition, the above description is just an example with n=2 or 3. In actual implementation, when n is a larger value, calculation can be performed in a similar calculation manner as described above, which is not repeated here.

At step 105, B-mode ultrasound echo data are acquired.

The ultrasound apparatus can also transmit pulses through the ultrasound probe to obtain the B-mode ultrasound echo data. Due to different requirements for the transmission pulses of the B-mode and the blood flow imaging mode, the B-mode data and the blood flow imaging mode data are acquired and processed differently, that is, B-mode ultrasound echo data and blood flow imaging mode echo can be obtained through different sequence pulses. For example, B-mode receiving lines and blood flow imaging mode receiving lines may be obtained alternately until a complete B-mode image and blood flow imaging mode image is obtained. Of course, in actual implementation, one frame of B-mode image and one frame of blood flow imaging mode image may also be obtained alternately. And to obtain a higher frame rate of the blood flow imaging mode, one frame of B-mode image and multiple frames of blood flow imaging mode images may be obtained alternately.

In actual implementation, when the B-mode ultrasound echo data are obtained, harmonic data or fundamental wave data can be obtained, which is not limited in this embodiment.

At step 106, scan conversion is performed on the B-mode ultrasound echo data and the calculated image gray intensity of the blood flow imaging mode, and an ultrasound image is displayed according to a conversion result.

In actual implementation, the B-mode ultrasound image and the blood flow imaging mode image can be displayed separately, and can also be displayed side by side, and of course, can also be displayed in combination. This embodiment is described by using an example of displaying a combination of the B-mode ultrasound echo data and the blood flow imaging mode image data, after acquiring the B-mode ultrasound echo data and the blood flow imaging mode image data. In this case, the step includes: combining the B-mode ultrasound echo data and the image of the blood flow imaging mode, and displaying the combined ultrasound image. In actual implementation, the ways of combining the images includes: determining brightness of the combined ultrasound image according to a magnitude relationship between brightness of the image of the blood flow imaging mode and a brightness threshold, and the B-mode ultrasound echo data.

Specifically:

First, brightness $X_B$ of a B-mode ultrasound image and brightness $X_{X\text{-}Flow}$ of the image of the blood flow imaging mode are acquired.

Second, it is determined that $X=X_B$ when $X_{S\text{-}Flow} \leq$ threshold$_{S\text{-}Flow}$ wherein X is the brightness of the combined image, wherein threshold$_{S\text{-}Flow}$ is a minimum brightness level threshold of the blood flow imaging mode, and signals below $threshold_{S-Flow}$ are all regarded as non-blood flow imaging mode signals.

Third, it is determined that $X=X_{S-Flow}+\alpha X_B/256$ when $X_{S-Flow}>threshold_{S-Flow}$, wherein $\alpha$ can be calculated as one of:

(a) $\alpha = (256 - (X_{S-Flow} - threshold_{S-Flow}))$;

(b) $\alpha = 255 - \sqrt{255^2 - (X_{S-Flow} - threshold_{S-Flow} - 255)^2}$; and (c) $\alpha = 255 / (X_{S-Flow} - threshold_{S-Flow})$.

Figure 4:
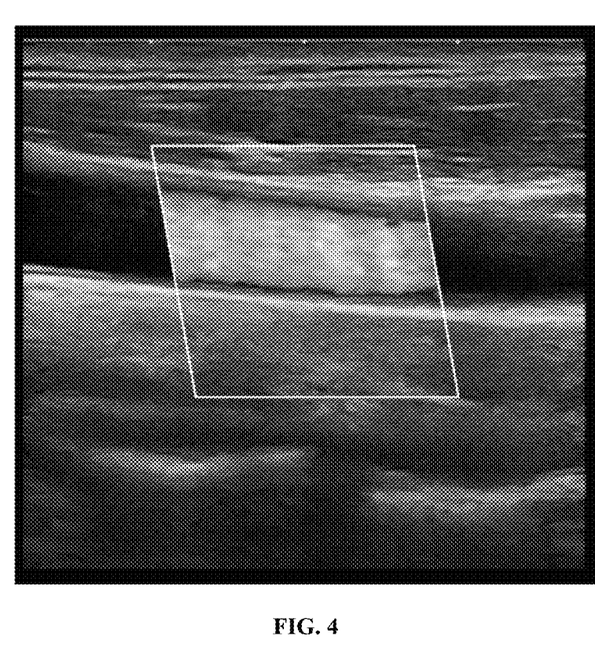
FIG. 4 is a schematic diagram of an ultrasound blood flow image obtained by using an existing method.
Figure 5:
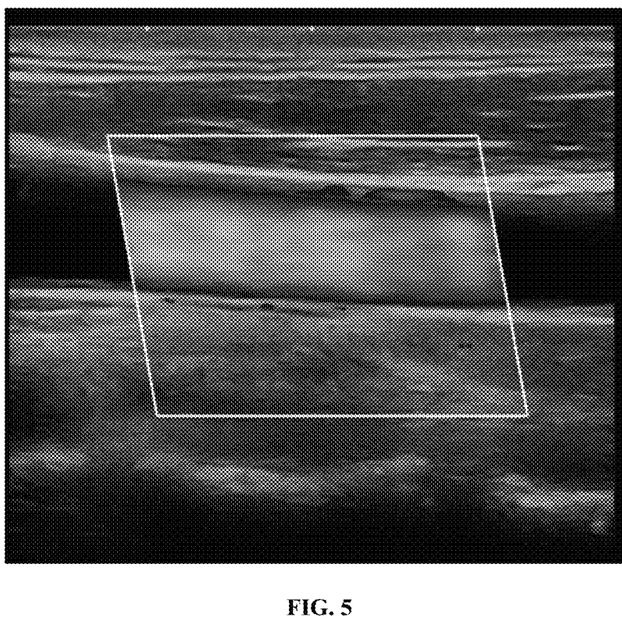
FIG. 5 is a schematic diagram of an ultrasound blood flow image obtained by using a method according to some embodiments of the present disclosure.

Referring to FIG. 4, which shows an ultrasound blood flow image obtained by using an existing method. As can be seen from FIG. 4, the obtained ultrasound blood flow image is not smooth enough and has artifacts to some degree. However, referring to FIG. 5, which shows an ultrasound blood flow image obtained by using the method of this embodiment, the ultrasound blood flow image obtained by using the method of this embodiment is obviously smoother, and artifacts are largely eliminated.

In summary, the ultrasound imaging device provided in this embodiment calculates the differential signal d(t) of the n echo signals and the sum B(t) of the envelopes of the echo signals, then calculates the image gray intensity of the blood flow imaging mode according to d(t) and B(t), and displays the ultrasound image according to the B-mode ultrasound echo data and the calculated image gray intensity during ultrasound imaging. In this way, the problem of artifacts in the ultrasound image in the prior art is solved, and artifacts in the image caused by tissue movement flickering and weak blood flow can be eliminated.

Moreover, in calculation of the image gray intensity in this embodiment, the difference between the logarithmic values of d(t) and B(t) is calculated to calculate the image gray intensity, thus achieving an effect of low processing complexity by simple subtraction while eliminating the artifacts.

This embodiment further provides an ultrasound device including: a memory and a processor, the memory storing at least one program instruction, and the processor loading and executing the at least one program instruction to implement the above-mentioned ultrasound imaging method.

This embodiment further discloses an ultrasound system including the above-mentioned ultrasound imaging device.

This embodiment further discloses a breast ultrasound apparatus including the ultrasound imaging device of the first aspect, the breast ultrasound apparatus being used to achieve the following functions:

transmitting ultrasound pulses to a breast area and receiving n echo signals in an interleaved transmission and reception manner in a blood flow imaging mode, wherein n is an integer greater than 1;

acquiring a differential signal d(t) of the n echo signals;

performing amplitude detection on the n echo signals to obtain an envelope of each echo signal, and acquiring a sum B(t) of the envelopes of the echo signals;

calculating image gray intensity of the blood flow imaging mode according to the d(t) and the B(t);

acquiring B-mode ultrasound echo data; and performing scan conversion on the B-mode ultrasound echo data and the calculated image gray intensity of the blood flow imaging mode, and displaying a breast ultrasound image according to a conversion result.

An embodiment of the present disclosure further provides a non-transitory computer readable storage medium that stores a set of computer executable instructions, and the computer executable instructions may be executed for performing the ultrasound imaging methods in any of the above method embodiments. The storage medium may be a magnetic disk, an optical disk, a read-only memory (ROM), a random-access memory (RAM), a flash memory, a hard disk drive (HDD), a solid-state drive (SSD), or the like; and the storage medium may also include a combination of the aforementioned types of memory.

Although the embodiments of the present disclosure are described with reference to the accompanying drawings, those skilled in the art can make various modifications and variations without departing from the spirit and scope of the present disclosure, and such modifications and variations fall within the scope defined by the appended claims.

The invention claimed is:

1. An ultrasound imaging device, comprising: a memory and a processor, the memory storing at least one program instruction, and the processor loading and executing the at least one program instruction to implement a method comprising the following steps:

transmitting ultrasound pulses and receiving n echo signals in an interleaved transmission and reception manner in a blood flow imaging mode, wherein n is an integer greater than 1;

acquiring a differential signal d(t) of the n echo signals;

performing amplitude detection on the n echo signals to obtain an envelope of each echo signal, and acquiring a sum B(t) of the envelopes of the echo signals;

calculating image gray intensity of the blood flow imaging mode according to the d(t) and the B(t);

acquiring B-mode ultrasound echo data; and performing scan conversion on the B-mode ultrasound echo data and the calculated image gray intensity of the blood flow imaging mode, and displaying an ultrasound image according to a conversion result.

2. The device according to claim 1, wherein the step of transmitting ultrasound pulses in an interleaved transmission and reception manner in a blood flow imaging mode comprises:

enabling transmission and reception of a j-th group of receiving lines, wherein an initial value of j is 1; and setting j+1 after the reception of the j-th group of receiving lines is completed, and executing the step of enabling transmission and reception of the j-th group of receiving lines immediately.

3. The device according to claim 1, wherein the step of calculating image gray intensity of the blood flow imaging mode according to the d(t) and the B(t) comprises:

updating the value of the B(t) according to a magnitude relationship between the B(t) and a preset threshold $N_{thold}$; and calculating image gray intensity of the blood flow imaging mode according to the d(t) and the updated B(t).

4. The device according to claim 3, wherein the step of updating the value of the B(t) according to a magnitude relationship between the B(t) and a preset threshold $N_{thold}$ comprises:

regarding $N_{thold}$ as the updated B(t) under the condition that $B(t)<-N_{thold}$.

5. The device according to claim 3, wherein the step of calculating image gray intensity of the blood flow imaging mode according to the d(t) and the updated B(t) comprises:

calculating image gray intensity of the blood flow imaging mode as $$\frac{|d(t)|}{|B(t)|};$$

or calculating image gray intensity of the blood flow imaging mode as log $$\log\frac{|d(t)|}{|B(t)|} = \log|d(t)| - \log|B(t)|.$$

6. The device according to claim 1, wherein the step of performing scan conversion on the B-mode ultrasound echo data and the calculated image gray intensity of the blood flow imaging mode, and displaying an ultrasound image according to a conversion result comprises:
 combining the B-mode ultrasound echo data and an image of the blood flow imaging mode, and displaying the combined ultrasound image;
 or
 displaying a B-mode ultrasound image according to the B-mode ultrasound echo data, and displaying a blood flow image according to the image gray intensity of the blood flow imaging mode.

7. The device according to claim 6, wherein the step of combining the B-mode ultrasound echo data and an image of the blood flow imaging mode, and displaying the combined ultrasound image comprises:
 determining brightness of the combined ultrasound image according to a magnitude relationship between brightness of the image of the blood flow imaging mode and a brightness threshold, and the B-mode ultrasound echo data.

8. The device according to claim 7, wherein the step of determining brightness of the combined ultrasound image according to a magnitude relationship between brightness of the image of the blood flow imaging mode and a brightness threshold, and the B-mode ultrasound echo data comprises:
 acquiring brightness $X_B$ of the B-mode ultrasound image and brightness $X_{S\text{-}Flow}$ of the image of the blood flow imaging mode;
 determining that $X=X_B$ when $X_{S\text{-}Flow} \leq \text{threshold}_{S\text{-}Flow}$, wherein X is the brightness of the combined ultrasound image; and
 determining that $X=X_{S\text{-}Flow}+\alpha X_B/256$ when $X_{S\text{-}Flow}>\text{threshold}_{S\text{-}Flow}$, wherein $\alpha$ is a coefficient,
 wherein $\text{threshold}_{S\text{-}Flow}$ is a minimum brightness level threshold of the blood flow imaging mode.

9. The device according to claim 8, wherein $\alpha$ is one of:

$$(a)\, \alpha = (256 - (X_{S\text{-}Flow} - \text{threshold}_{S\text{-}Flow}));$$

$$(b)\, \alpha = 255 - \sqrt{255^2 - (X_{S\text{-}Flow} - \text{threshold}_{S\text{-}Flow} - 255)^2}; \text{ and}$$

$$(c)\, \alpha = 255 / (X_{S\text{-}Flow} - \text{threshold}_{S\text{-}Flow}).$$

10. The device according to claim 1, wherein the method further comprises:
 obtaining B-mode receiving lines and blood flow imaging mode receiving lines alternately until a complete B-mode image and blood flow imaging mode image is obtained when the n echo signals and the B-mode ultrasound echo data are acquired;
 or
 obtaining one frame of B-mode image and multiple frames of blood flow imaging mode images alternately when the n echo signals and the B-mode ultrasound echo data are acquired.

11. An ultrasound system, comprising the ultrasound imaging device of claim 1.

12. A breast ultrasound apparatus, comprising the ultrasound imaging device of claim 1, the breast ultrasound apparatus being used to achieve the following functions:
 transmitting ultrasound pulses to a breast area and receiving n echo signals in an interleaved transmission and reception manner in a blood flow imaging mode, wherein n is an integer greater than 1;
 acquiring a differential signal d(t) of the n echo signals;
 performing amplitude detection on the n echo signals to obtain an envelope of each echo signal, and acquiring a sum B(t) of the envelopes of the echo signals;
 calculating image gray intensity of the blood flow imaging mode according to the d(t) and the B(t);
 acquiring B-mode ultrasound echo data; and
 performing scan conversion on the B-mode ultrasound echo data and the calculated image gray intensity of the blood flow imaging mode, and displaying a breast ultrasound image according to a conversion result.

13. A method for using an ultrasound imaging device, comprising the following steps:
 transmitting ultrasound pulses and receiving n echo signals in an interleaved transmission and reception manner in a blood flow imaging mode, wherein n is an integer greater than 1;
 acquiring a differential signal d(t) of the n echo signals;
 performing amplitude detection on the n echo signals to obtain an envelope of each echo signal, and acquiring a sum B(t) of the envelopes of the echo signals;
 calculating image gray intensity of the blood flow imaging mode according to the d(t) and the B(t);
 acquiring B-mode ultrasound echo data; and
 performing scan conversion on the B-mode ultrasound echo data and the calculated image gray intensity of the blood flow imaging mode, and displaying an ultrasound image according to a conversion result.

14. The method according to claim 13, wherein the step of transmitting ultrasound pulses in an interleaved transmission and reception manner in a blood flow imaging mode comprises:
 enabling transmission and reception of a j-th group of receiving lines, wherein an initial value of j is 1; and
 setting j+1 after the reception of the j-th group of receiving lines is completed, and executing the step of enabling transmission and reception of the j-th group of receiving lines immediately.

15. The method according to claim 13, wherein the step of calculating image gray intensity of the blood flow imaging mode according to the d(t) and the B(t) comprises:
 updating the value of the B(t) according to a magnitude relationship between the B(t) and a preset threshold $N_{thold}$; and
 calculating image gray intensity of the blood flow imaging mode according to the d(t) and the updated B(t).

16. The method according to claim 15, wherein the step of updating the value of the B(t) according to a magnitude relationship between the B(t) and a preset threshold $N_{thold}$ comprises:
 regarding $N_{thold}$ as the updated B(t) under the condition that $B(t)<N_{thold}$.

17. The method according to claim 15, wherein the step of calculating image gray intensity of the blood flow imaging mode according to the d(t) and the updated B(t) comprises:

calculating image gray intensity of the blood flow imaging mode as $$\frac{|d(t)|}{|B(t)|};$$

or calculating image gray intensity of the blood flow imaging mode as log $$\log\frac{|d(t)|}{|B(t)|} = \log|d(t)| - \log|B(t)|.$$

18. The method according to claim 13, wherein the step of performing scan conversion on the B-mode ultrasound echo data and the calculated image gray intensity of the blood flow imaging mode, and displaying an ultrasound image according to a conversion result comprises:

combining the B-mode ultrasound echo data and an image of the blood flow imaging mode, and displaying the combined ultrasound image;

or displaying a B-mode ultrasound image according to the B-mode ultrasound echo data, and displaying a blood flow image according to the image gray intensity of the blood flow imaging mode.

19. The method according to claim 18, wherein
the step of combining the B-mode ultrasound echo data and an image of the blood flow imaging mode, and displaying the combined ultrasound image comprises:
determining brightness of the combined ultrasound image according to a magnitude relationship between brightness of the image of the blood flow imaging mode and a brightness threshold, and the B-mode ultrasound echo data.

20. A non-transitory computer-readable storage medium, storing a computer program, wherein when the computer program is executed by a processor, the steps of the method according to claim 13 are implemented.

* * * * *

UNITED STATES PATENT AND TRADEMARK OFFICE
CERTIFICATE OF CORRECTION

PATENT NO. : 12,089,998 B2
APPLICATION NO. : 17/423175
DATED : September 17, 2024
INVENTOR(S) : Hong Wang et al.

Page 1 of 1

It is certified that error appears in the above-identified patent and that said Letters Patent is hereby corrected as shown below:

In the Claims

In Claim 4, Column 12, Line 62, "B(t)<–N$_{thold}$." should read --B(t)<N$_{thold}$.--.

In Claim 5, Column 13, Lines 7-8, after "blood flow imaging mode as", delete "log".

In Claim 9, Column 13, Line 55, before "$\alpha = (256 - (X_{S-Flow} - threshold_{S-Flow}))$;", delete "(a)".

In Claim 9, Column 13, Line 57, before "$\alpha = 255 - \sqrt{255^2 - (X_{S-Flow} - threshold_{S-Flow} - 255)^2}$ ;", delete "(b)".

In Claim 9, Column 13, Line 58, before "α = 255/($X_{S-Flow}$ – threshold$_{S-Flow}$).", delete "(c)".

In Claim 10, Column 13, Lines 64-66, "a complete B-mode image and blood flow imaging mode image is obtained" should read --a complete B-mode image and blood flow imaging mode image are obtained--.

In Claim 17, Column 15, Lines 14-15, after "blood flow imaging mode as", delete "log".

Signed and Sealed this
Seventh Day of October, 2025

John A. Squires
*Director of the United States Patent and Trademark Office*